United States Patent
Gindelberger et al.

(10) Patent No.: US 10,556,889 B1
(45) Date of Patent: Feb. 11, 2020

(54) SALVINORIN DERIVATIVES

(71) Applicant: Blue Sky Pharmaceuticals, LLC, Ballwim, MO (US)

(72) Inventors: David Gindelberger, Ladue, MO (US); John J. Talley, St. Louis, MO (US)

(73) Assignee: Blue Sky Pharmaceuticals, LLC, Ballwin, MO (US)

(*) Notice: Subject to any disclaimer, the term of this patent is extended or adjusted under 35 U.S.C. 154(b) by 0 days.

(21) Appl. No.: 16/371,283

(22) Filed: Apr. 1, 2019

Related U.S. Application Data

(60) Provisional application No. 62/781,976, filed on Dec. 19, 2018.

(51) Int. Cl.
*C07D 407/04* (2006.01)
*C07D 417/14* (2006.01)
*A61P 25/04* (2006.01)
*C07D 405/14* (2006.01)
*C07D 409/04* (2006.01)
*C07D 413/14* (2006.01)

(52) U.S. Cl.
CPC .......... *C07D 407/04* (2013.01); *A61P 25/04* (2018.01); *C07D 405/14* (2013.01); *C07D 409/04* (2013.01); *C07D 413/14* (2013.01); *C07D 417/14* (2013.01)

(58) Field of Classification Search
CPC .. C07D 407/04; C07D 405/14; C07D 409/04; C07D 413/14; C07D 417/14; A61P 25/04
USPC ........................................................ 549/280
See application file for complete search history.

(56) References Cited

U.S. PATENT DOCUMENTS

| 2006/0058264 A1* | 3/2006 | Prisinzano | C07D 311/92 514/63 |
| 2007/0213394 A1* | 9/2007 | Beguin | C07D 307/40 514/455 |
| 2009/0088466 A1* | 4/2009 | Bohn | C07D 311/92 514/455 |
| 2017/0313692 A1* | 11/2017 | Prisinzano | G01N 33/9486 |

FOREIGN PATENT DOCUMENTS

WO  WO-2005089745 A1 * 9/2005 ............ C07D 307/40

OTHER PUBLICATIONS

Crowley; J. Med. Chem. 2016, 59, 24, 11027-11038. (Year: 2016).*
Groer; Mol Pharmacol. 2007, 71, 549-557. (Year: 2007).*
Kane; J. Med. Chem. 2008, 51, 6, 1824-1830. (Year: 2008).*
Tidgewell; Journal of Natural Products 2006, 69, 914-918. (Year: 2006).*
Tidgewell; J. Med. Chem. 2008, 51, 8, 2421-2431. (Year: 2008).*
Chavkin; Journal of Pharmacology and Experimental Therapeutics 2004, 308, 1197-1203. (Year: 2004).*
Lee; Bioorganic & Medicinal Chemistry Letters 15 (2005) 3744-3747. (Year: 2005).*
Harding; J. Med. Chem. 2005, 48, 4765-4771. (Year: 2005).*
Beguin; Bioorganic & Medicinal Chemistry Letters 15 (2005) 2761-2765. doi:10.1016/j.bmcl.2005.03.113 (Year: 2005).*
McGovern; Journal of Molecular Graphics and Modelling 28 (2010) 612-625. doi:10.1016/j.jmgm.2009.12.008 (Year: 2010).*

* cited by examiner

*Primary Examiner* — Daniel R Carcanague
(74) *Attorney, Agent, or Firm* — Husch Blackwell LLP

(57) ABSTRACT

Provided herein is a compound of Formula I, or a salt thereof,

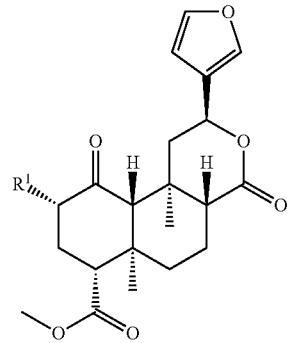

wherein $R^1$ is a moiety having the following structure:

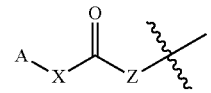

wherein Z is selected from the group consisting of O and N; X is selected from the group consisting of a bond, NH, and C(O)NH; and A is selected from the group consisting of substituted aryl and substituted heteroaryl. Compounds of Formula I are useful as opioid receptor agonists. Because the compounds exhibit relatively low levels of β-arrestin recruitment, they do not produce the negative side effects commonly associated with morphine-derived compounds.

29 Claims, No Drawings

SALVINORIN DERIVATIVES

CROSS-REFERENCE TO RELATED APPLICATIONS

This application claims the benefit of U.S. Provisional Application No. 62/781,976, filed Dec. 19, 2018, which is hereby incorporated by reference in its entirety.

BACKGROUND

Traditional opiate receptor agonists such as morphine and fentanyl interact strongly with the μ-opioid receptor present on the surface of several types of cells in the human body. Large and/or repeated doses of a typical μ-opioid receptor agonist result in activation of a pathway to modulate the stimulus, reducing its effectiveness. The modulation pathway involves interaction of the intracellular portion of the receptor with a family of proteins called arrestins. Interaction of the arrestin with the internal portion of the receptor blocks the interaction of other molecules and stops the normal cascade of activity in the cell. In addition to this modulation, the arrestins cause the receptor to "internalize" or pucker so that it is more difficult for extracellular molecule to dock with the receptor. This modulation effectively reduces the efficacy of the drug, leading to the requirement for higher doses to achieve the same level of pain reduction.

Accordingly, it is desirable to develop alternatives to existing pain relief formulations that provide effective control of pain with lower potential for addiction. It is also desirable to identify alternative active compounds that are effective at relatively low doses of the active ingredient and are economical to incorporate into stable pharmaceutical formulations.

Salvinorin, also known as Salvinorin A, is a psychotropic molecule found naturally in *Salvia divinorum* and having the following structure.

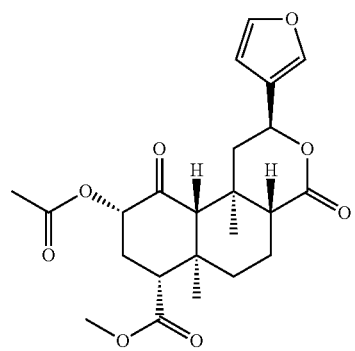

A limited amount of research has been performed to identify salvinorin derivatives that may be useful for the treatment of pain. For example, U.S. Pat. No. 7,728,001 to Prisinzano et al. described a class of salvinorin derivatives that were claimed to be opioid receptor ligands. U.S. 2017/0313692 A1 by Prisinzano identified a much smaller class of salvinorin-derived compounds that are μ-opioid receptor agonists and were claimed to exhibit a significant reduction of the negative side effects commonly associated with morphine-derived compounds. In general, however, the potential of salvinorin derivative compounds to provide effective pain relief without the undesirable side effects associated with traditional opiate receptor agonists has not been studied in great detail.

SUMMARY

Provided herein is a compound of Formula I, or a salt thereof,

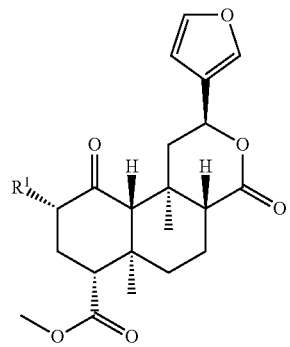

wherein $R^1$ is a moiety having the following structure:

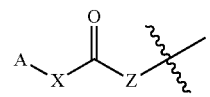

wherein Z is selected from the group consisting of O and N; X is selected from the group consisting of a bond, NH, and C(O)NH; and A is selected from the group consisting of substituted aryl and substituted heteroaryl.

Also provided herein is a pharmaceutical composition comprising a compound as provided herein (e.g., a compound of Formula I).

Also provided herein is a method of treating pain in a mammal, the method comprising administering a pharmaceutical composition as provided herein to a mammal having said pain.

DETAILED DESCRIPTION

Provided herein are compounds that are derivatives of Salvinorin A. Generally, the compounds described herein correspond to a Salvinorin A molecule wherein one of the acetoxy groups is replaced by a novel moiety.

The compounds provided herein are potent μ-opioid agonists and, accordingly, are effective as pain relief agents. The compounds provided herein also exhibit relatively low levels of recruitment of the β-arrestin receptor, which is responsible for many of the negative side effects commonly associated with morphine-derived compounds. Accordingly, compounds provided herein may provide effective pain relief without the undesirable side effects associated with traditional opiate receptor agonists.

For example, provided herein is a compound of Formula I, or a salt thereof,

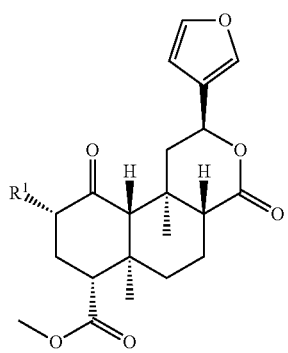

Formula I wherein R¹ is a moiety having the following structure:

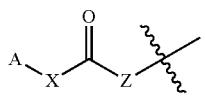

wherein Z is selected from the group consisting of O and N; X is selected from the group consisting of a bond, NH, and N(H)C(O); and A is selected from the group consisting of substituted aryl and substituted heteroaryl.

In preferred embodiments, X is selected from the group consisting of a bond and NH. For example, X can be NH. In preferred embodiments, Z is O.

In preferred embodiments, A is a substituted 5-membered or 6-membered aryl or heteroaryl. For example, A can be selected from the group consisting of phenyl, pyridyl, pyrimidyl, pyrazyl, thiazyl, thienyl, isoxazolyl, oxazolyl, and furanyl, each of which is preferably substituted. Non-limiting examples of preferred substituents include halogen, $CH_3$, CN, $O(CHF_2)$, $CF_3$, $OCH_3$, and $OCF_3$. Most preferably, the aryl or heteroaryl comprises a substituent in the trans position, for example at the 4-position for a 6-membered ring, and at the 3-position or 4-position for a 5-membered ring. In some embodiments, the aryl or heteroaryl comprises two or more substitutents, one of which is at the trans position of the ring as described above.

For example, the compound of Formula I may be a compound of Formula Ia or a salt thereof,

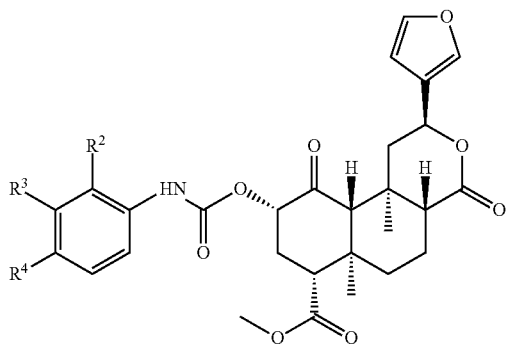

Formula Ia wherein
$R^2$ and $R^3$ are each independently selected from the group consisting of hydrogen and halogen;

and $R^4$ is selected from the group consisting of hydrogen, halogen, $CH_3$, CN, $O(CHF_2)$, $CF_3$, $OCH_3$, and $OCF_3$.

In preferred embodiments, at least one of $R^2$ and $R^3$ is hydrogen. For example, both $R^2$ and $R^3$ can be hydrogen. Preferably, $R^4$ is selected from the group consisting of Cl, F, $CH_3$, CN, $O(CHF_2)$, and $CF_3$.

Alternatively, the compound of Formula I may be a compound of Formula Ib or a salt thereof,

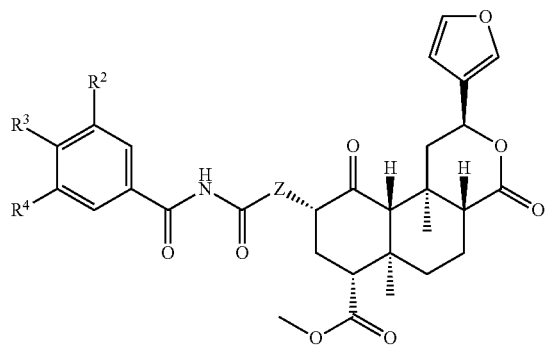

Formula Ib wherein $R^2$, $R^3$, and $R^4$ are each independently selected from the group consisting of hydrogen, halogen, $CH_3$, CN, $O(CHF_2)$, $CF_3$, $OCH_3$, and $OCF_3$, and Z is selected from the group consisting of O and N. For example, $R^2$, $R^3$, and $R^4$ can each be hydrogen.

As a further example, the compound of Formula I may be a compound of Formula Ic or a salt thereof,

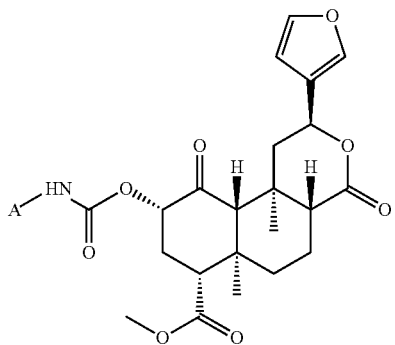

Formula Ic wherein A is a heteroaryl selected from the group consisting of phenyl, pyridyl, pyrimidyl, pyrazyl, thiazyl, thienyl, isoxazolyl, oxazolyl, and furanyl, each of which may be optionally substituted as described above.

In preferred embodiments, A is a substituted heteroaryl selected from the group consisting of pyridyl, pyrimidyl, pyrazyl, thiazyl, thienyl, and isoxazolyl, each of which is substituted in the trans position as described above. Non-limiting examples of preferred substituents include halogen, $CH_3$, CN, $O(CHF_2)$, $CF_3$, $OCH_3$, and $OCF_3$.

As a further example, the compound of Formula I may be a compound of Formula Id or a salt thereof, Formula Id

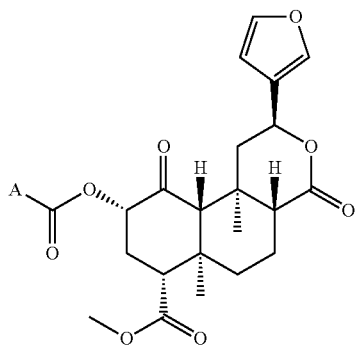

wherein A is a heteroaryl selected from the group consisting of phenyl, pyridyl, pyrimidyl, pyrazyl, thiazyl, thienyl, isoxazolyl, oxazolyl, and furanyl, each of which may be optionally substituted as described above.

In preferred embodiments, A is a substituted heteroaryl selected from the group consisting of phenyl, pyridyl, pyrimidyl, pyrazyl, thiazyl, thienyl, and isoxazolyl, each of which is substituted in the trans position as described above. Non-limiting examples of preferred substituents include halogen, $CH_3$, CN, $O(CHF_2)$, $CF_3$, $OCH_3$, and $OCF_3$.

The compounds provided herein are potent and effective μ-opioid receptor agonists. Preferred compounds provided herein exhibit an efficacy similar to that of DAMGO (a standard μ-opioid receptor agonist known to those skilled in the art). For example, preferred compounds as described herein are μ-opioid receptor agonists having an efficacy at least about 80%, at least about 90%, or at least about 95% as compared to DAMGO. Preferably, the compounds provided herein have a potency of less than about 1000 nM, less than about 900 nM, less than about 800 nM, less than about 700 nM, less than about 600 nM, or even less than about 500 nM when evaluated using the experimental procedure described in Example 2 below.

Additionally, the compounds provided herein exhibit relatively low levels of recruitment of the β-arrestin receptor. Preferred compounds provided herein exhibit a mean β-arrestin recruitment $EC_{50}$ of at least about 9 μM, and preferably in excess of 10 μM. Particularly preferred compounds provided herein will also exhibit a β-arrestin recruitment maximum-fold efficacy signal versus background of less than about 10, less than about 8, less than about 7, less than about 6, or even less than about 5.

Non-limiting examples of species include Formula Ia-i, or a salt thereof,

Formula Ia-i

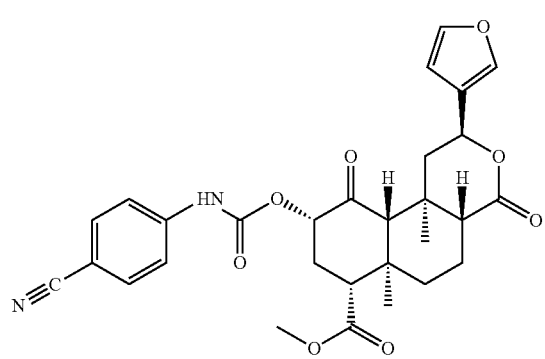

Formula Ia-ii, or a salt thereof,

Formula Ia-ii

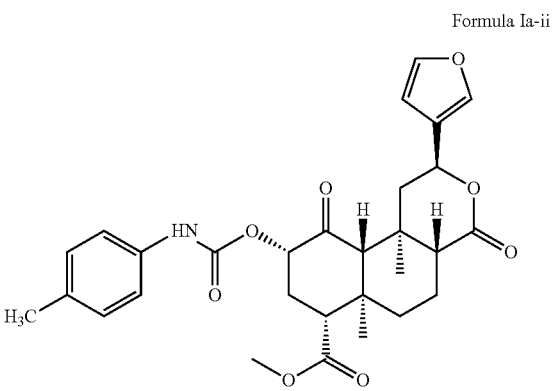

Formula Ia-iii, or a salt thereof,

Formula Ia-iii

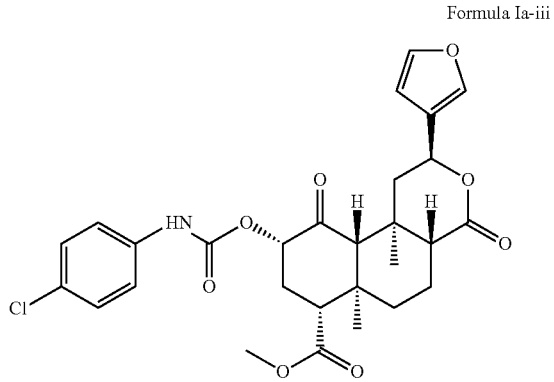

Formula Ia-iv, or a salt thereof,

Formula Ia-iv

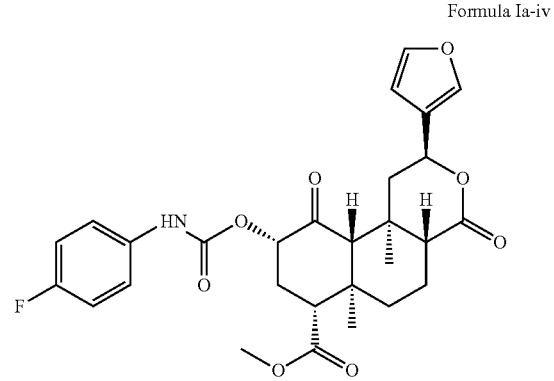

Formula Ia-v, or a salt thereof,
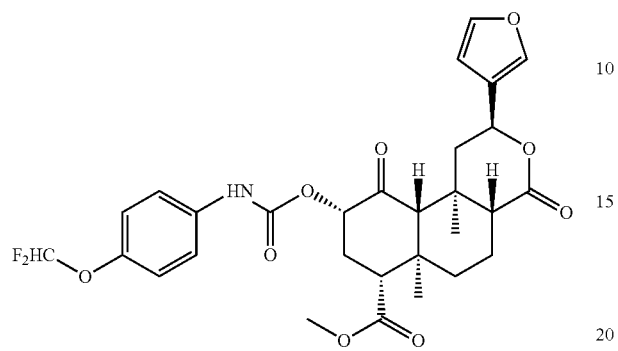
Formula Ia-v
Formula Ia-vi, or a salt thereof,
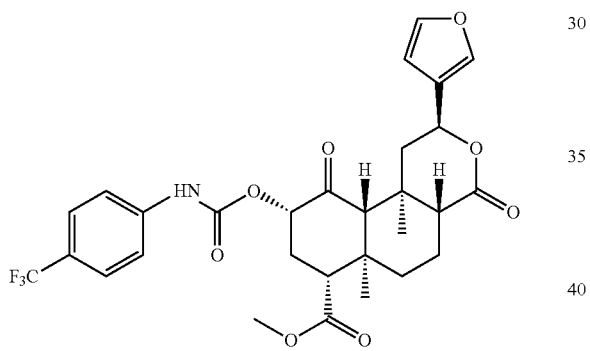
Formula Ia-vi
Formula Ia-vii, or a salt thereof,
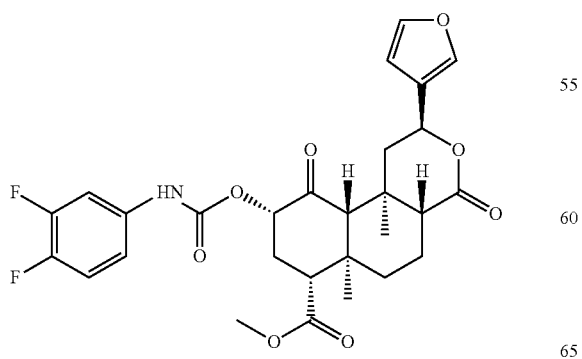
Formula Ia-vii
Formula Ia-viii, or a salt thereof,
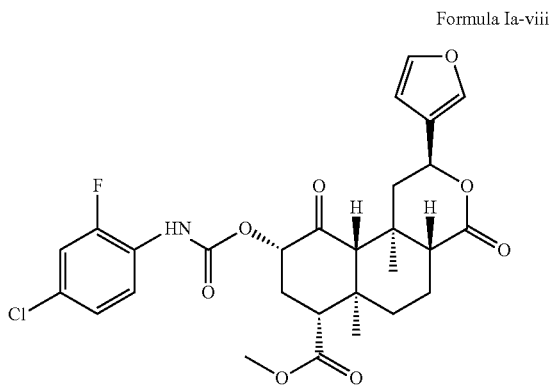
Formula Ia-viii
Formula Ib-i, or a salt thereof,
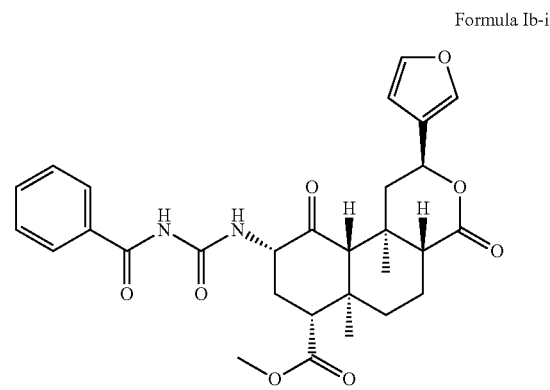
Formula Ib-i
Formula Ib-ii, or a salt thereof,
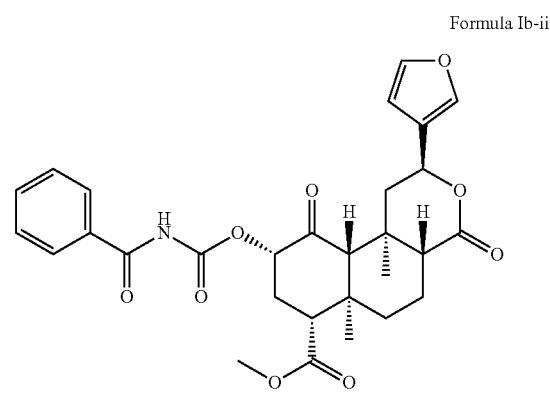
Formula Ib-ii Formula Ic-i, or a salt thereof,
Formula Ic-i
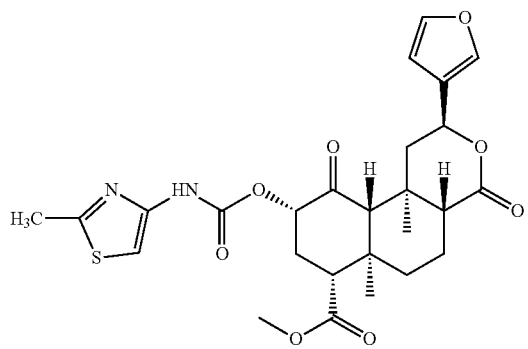
Formula Ic-ii, or a salt thereof,
Formula Ic-ii
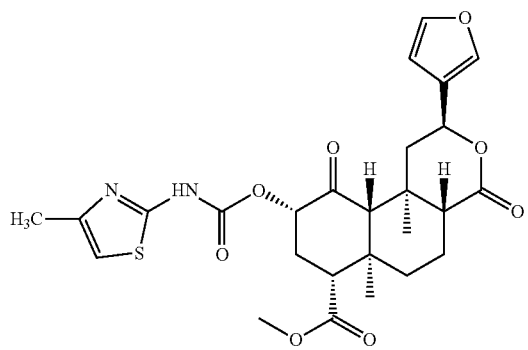
Formula Ic-iii, or a salt thereof,
Formula Ic-iii
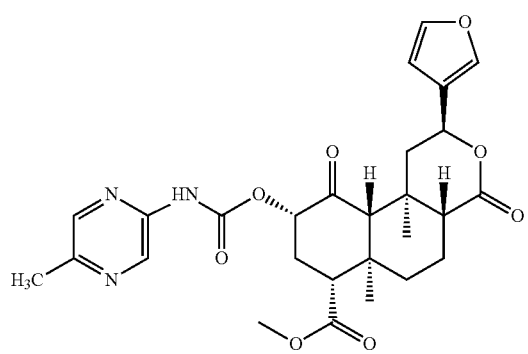
Formula Ic-iv, or a salt thereof,
Formula Ic-iv
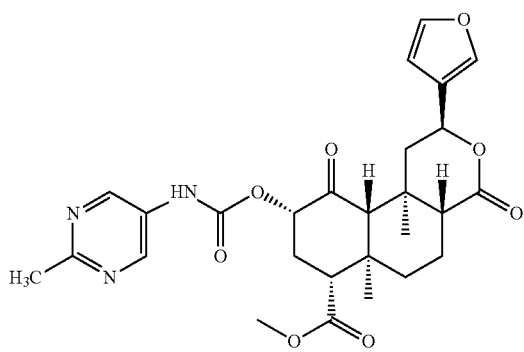
Formula Ic-v, or a salt thereof,
Formula Ic-v
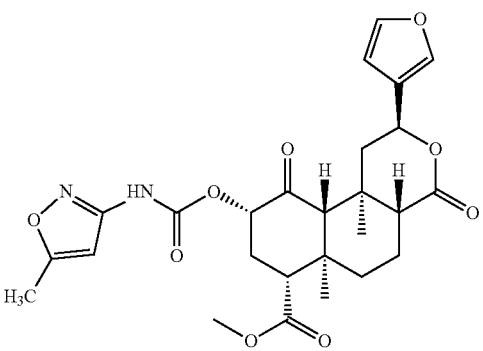
Formula Id-i, or a salt thereof,
Formula Id-i
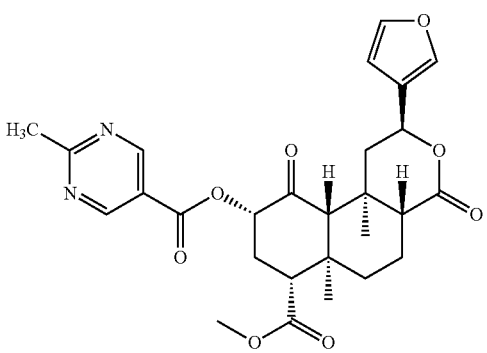

Formula Id-ii, or a salt thereof,

Formula Id-ii

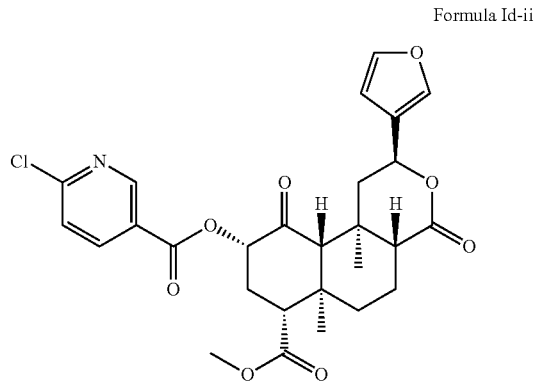

and Formula IId-iii, or a salt thereof.

Formula IId-iii

As used herein, the term "hydrogen" includes both stable isotopes of hydrogen, namely $^1$H (also known as protium) and $^2$H (also known as deuterium).

As used herein, the term "halogen" refers to a halogen atom selected from the group consisting of fluorine, chlorine, bromine, and iodine. In preferred embodiments, the halogen is selected from the group consisting of fluorine and chlorine. For example, the halogen can be fluorine. Alternatively, the halogen can be chlorine.

As used herein, the term "alkoxy" refers to a group of the form —OR', wherein R' is selected from the group consisting of $C_1$-$C_6$ alkyl. For example, the group —OCH$_3$ may be referred to herein as "methoxy." The group —OCH$_2$CH$_3$ may be referred to herein as "ethoxy."

As used herein, the term "carboxyl" refers to a group of the form —C(O)OH.

As used herein, the term "amido" refers to a group of the form —C(O)NH$_2$ or —C(O)NH—.

As used herein, the term "acetoxy" refers to a group of the form —C(O)OCH$_3$.

Pharmaceutical Compositions

Also provided herein is a pharmaceutical composition comprising a compound of Formula I (e.g., a compound of Formula I, Formula Ia, Formula Ib, Formula Ic, or Formula Id) as described herein.

Generally, the pharmaceutical composition may comprise one or more compounds as described herein. For example, the composition may comprise two or more compounds as described herein.

The pharmaceutical composition can comprise one or more pharmaceutically acceptable excipients. Suitable excipients are generally known to those skilled in the art.

The pharmaceutical composition can generally comprise any dosage form known in the art. For example, the composition can be in the form of a tablet, capsule, granulated powder, or gel. As further non-limiting examples, the composition can be in the form of a liquid suspension, emulsion, or aqueous solution.

Methods of Treatment

Also provided herein is a method of treating pain in a mammal. The mammal may be, for example, a human. Generally, the method comprises administering a pharmaceutical composition as described herein (i.e., a composition comprising a compound of Formula I, Ia, Ib, Ic, or Id) to a mammal in need of treatment for pain.

Other objects and features will be in part apparent and in part pointed out hereinafter.

EXAMPLES

The following non-limiting examples are provided to further illustrate the present disclosure.

Example 1: Synthesis of Compounds of Formula I

The compounds of Formula I were synthesized using typical techniques that are known to those skilled in the art. The starting material utilized to synthesize all compounds of Formula I listed herein was Salvinorin B, which was obtained via hydrolysis of Salvinorin A. The Salvinorin B was then reacted with the desired acid chloride or isocyanate in the presence of a catalytic amount of DMAP. Purification of the reaction product was achieved using column chromatography under prep-scale reverse-phase conditions. Analytical methods used to verify the identity of the synthesized compounds included HPLC, mass spectrometry, and high field NMR.

Example 2: Efficacy and β-Arrestin Affinity Testing

Compounds of Formula I, prepared as described above, were tested to determine (1) their efficacy as pain relief agents and (2) their recruitment of the β-arrestin receptor, which is responsible for many of the negative side effects commonly associated with morphine-derived compounds.

The data provided in Tables 1A and 1B below were obtained using standard analytical techniques known to those skilled in the art. Such techniques are described in detail in C. E. Groer et al., Mol Pharmacol. 2007 February; 71(2): 549-557, and are summarized below.

Phospho-ERK 1/2

Agonist induced ERK 1/2 phosphorylation was measured in cultured HEK-293 cells containing uOR receptor. Total protein was extracted after induction and separated electrophoretically using SDS gel electrophoresis. Proteins were then transferred to polyvinylidene fluoride (PVDF) membranes and immunoblotted with phosphor ERK antibodies to determine the level of phosphorylation. Blots were then stripped and blotted for total ERK 1/2 levels.

MEF (mouse embryonic fibroblasts) that were lacking beta-arrestins 1 and 2 were used as controls for cell trafficking experiments. ERK activation studies were performed in parallel to trafficking studies to assure activity of the agonists.

Phosphorylated uOR

HEK-293 cells stably expressing uOR were stimulated with saline, morphine or herkinorin. After washing, cells were lysed in SDS/detergent buffer and centrifuged to remove debris. Solubilized protein was incubated overnight with monoclonal anti-hemmaglutin (HA)-agarose beads. The immunoprecipitated complex was collected and washed; proteins were then eluted and resolved on SDS gels. After transfer to PVDF membranes, immunoblotting was performed with a phospho-mOR antibody that recognized phosphorylation of Serine 375 on mOR. Membranes were then stripped and the total mOR was determined using a primary antibody against the C-terminus of the uOR. The degree of stimulation was determined by comparing the phosphor uOR to the total uOR.

Cross-Linking and Coimmunoprecipitation

HEK-293 cells tably expressing the uOR tagged at the H terminus were treated with either vehicle (1 uM DAMGO) or 10 uM herkinorin. The cross-linking reagent dithiobissuccinimidylpropionate [DSP] was added to perform the cross-linking reaction. After 20 minutes of incubation, the cross-linking reaction was stopped with orthovanadate. Cells were solubilized overnight and centrifuged to remove debris. Agarose beads coated with Anti-HA antibody to pull down the HA tagged muOR. Proteins were solubilized, and run on SDS Gels for resolution, followed by immunoblotting to PVDF membranes. A1CT antibody was used to detect beta-arrestins 1 and 2. Controls included reprobing the blots for equal pull-down of uOR lysates of HEK cells transfected with HA-uOR for uOR immunoblotting, and mouse cells (MEF wild type and knock-outs) for beta-arrestin immunoblotting.

Cellular Trafficking

HEK-29 cells were transiently transfected (electroporation) with combinations of cDNA for hemagglutinin (HA-N terminus)-tagged uOR, beta-arrestin2 tagged with green fluorescent protein, mouse uOR tagged at the C terminus with yellow fluorescent protein and GRK-2. (in some cases, cell stably expressing the uOR were used, and now differences were observed compared with transiently transfected cells). After addition of drug, cells were visualized using confocal microscopy. Multiple cells were recorded per dish after more than four separate transfection experiments— representative cells are shown in the manuscript.

Immunofluorescence of Cell Surface Receptors

Stably transfected HA-N terminus-tagged uOR-expressing HEK-293 cells were treated with either DAMGP or herkinorin. After fixation with paraformaldehyde, cells were incubated with an anti-HA antibody, and incubated with Alexa Fluor 488 anti-mouse secondary antibody. Immunofluorescence was assessed for DAMGO and herkinorin treated cells, and normalized against untreated cells. Nonspecific secondary antibody interactions were subtracted from each point. Cells were also treated similarly in parallel to this experiment with confocal dishes, followed by analysis with confocal microsply.

Biotinylated Receptor Internalization

HEK-293 cells stably expressing the iuOR tagged at the N terminus with HA were use for cell surface biotinylation experiments. After treatment with sulfo-NHS-SS-biotin, cells were divided into identical aliquots for assessment. For drug treatment cells were resuspended in MEM continaing either DMSO vehicle, DAMGO or herkinorin. After incubation, surface biotinylatoin was stripped away with glutathione stripping solution followed by quenching with iodoacetamide buffer. Cells were suspended, solubilized and centrifuged—the clear lysates were immunoprecipitated with avidin-conjugated agarose beads. Proteins were extracted from the immunoprecipitates and run on SDS gels, followed by immunoblotting with rabbit antibody directed to the C-terminus of uOR. The blots were treated with donkey anti-rabbit secondary antibody and then detected using enhanced chemiluminescence. Several controls were performed: 1) "100%" refers to total surface receptors and represents cells lysed directly after biotinylation and washes; 2) "strip" refers to cells that have been biotinylated and then stripped—this serves as control for the effectiveness of the glutathione stripping solution; 3) "mock" is the same as 100% but for cells that are stably mock-transfected with empty vector (no uOR); and 4) "no protein" refers to immunoprecipitation in the absence of the cellular lysate.

d

Experimental Results

In Tables 1A and 1B below, the "Efficacy" column lists the efficacy of the tested compound relative to DAMGO, which is a synthetic opioid peptide with high μ-opioid receptor efficacy, and is widely used in the art as a standard reference molecule. The term "efficacy" in this context refers to the magnitude of the downstream phosphorylation of MAP Kinases (ERK1/ERK2) after binding of the DAMGO or other molecules to the uOR (in an antagonistic reversible manner). An efficacy of 100% indicates that the efficacy of the tested compound was equivalent to DAMGO.

The "Potency" column in Tables 1A and 1B below indicates the amount of the tested compound required to produce a desired level of effect—in this case, the effect obtained by administration of 1.01 nM of DAMGO or 5.29 nM of morphine. A smaller potency value indicates that a smaller amount of the compound can be used to achieve efficacy similar or equal to DAMGO or Morphine. Conversely, compounds with a larger potency value will require administration of greater amounts to achieve a desired effect. The related column "SEM" refers to the standard error of the mean, and "N" refers to the total number of measurements that were taken in accordance with the experimental procedure described above.

TABLE 1A

| Standard Opioid Receptor Agonists | | | | | |
| --- | --- | --- | --- | --- | --- |
| Formula | R[1] | Efficacy | Potency (nM) | SEM (nM) | N |
| — | Met-Enkephalin | 101% | 0.674 | 0.10 | 6 |
| — | DAMGO | 100% | 1.01 | 0.06 | 49 |
| — | Morphine | 101% | 5.29 | 1.02 | 13 |

TABLE 1B

| | | | | SEM | |
|---|---|---|---|---|---|
| Formula | R¹ | Efficacy | Potency (nM) | (nM) | N |
| — | benzamide structure | 91% | 0.2323 | 0.2314 | 4 |
| Ia-i | 4-cyanophenyl carbamate structure | 97% | 35.52 | 13.27 | 5 |
| Ia-ii | 4-methylphenyl carbamate structure | 97% | 107.6 | 41.53 | 5 |
| Ia-iii | 4-chlorophenyl carbamate structure | 97% | 145.7 | 36.17 | 5 |
| Ia-iv | 4-fluorophenyl carbamate structure | 93% | 156.2 | 63.32 | 4 |
| Ia-v | 4-(difluoromethoxy)phenyl carbamate structure | 100% | 162.5 | 23.93 | 3 |
| Ia-vi | 4-(trifluoromethyl)phenyl carbamate structure | 94% | 327.3 | 102.9 | 7 |
| Ia-vii | 3,4-difluorophenyl carbamate structure | 97% | 411.8 | 107.8 | 2 |
| Ia-viii | 2-fluoro-4-chlorophenyl carbamate structure | 97% | 521.6 | 23.9 | 2 |
| Ib-i | benzoyl urea structure | 102% | 609.6 | 285.6 | 2 |

TABLE 1B-continued

Salvinorin Derivatives

| Formula | R¹ | Efficacy | Potency (nM) | SEM (nM) | N |
|---|---|---|---|---|---|
| Ib-ii | benzoyl carbamate (PhC(O)NHC(O)O–) | 102% | 632.9 | 255.3 | 3 |
| — | 4-(trifluoromethyl)benzoate | 95% | 930 | 237.6 | 4 |
| — | benzoate | 97% | 1111 | 99.11 | 12 |
| — | phenylcarbamate (PhNHC(O)O–) | 95% | 1198 | 240.5 | 2 |
| — | 4-fluorobenzoate | 105% | 1638 | 277 | 6 |
| — | 3,4-dichlorophenylcarbamate | 88% | 1853 | 169 | 2 |
| — | 4-(trifluoromethylthio)phenylcarbamate | 87% | 2304 | 396 | 2 |
| — | 4-methoxybenzoate | 96% | 3496 | 354.9 | 3 |
| — | (4-cyanophenyl)aminocarbonylamino | 97% | 4291 | 790 | 2 |
| — | 4-bromobenzoate | 92% | 6848 | 724 | 2 |

TABLE 1B-continued

Salvinorin Derivatives

| Formula | R¹ | Efficacy | Potency (nM) | SEM (nM) | N |
|---|---|---|---|---|---|
| — | 4-chlorophenylsulfonyl urea derivative | 94% | >10 μM | N/A | 2 |
| Ic-i | 2-methylthiazol-4-yl carbamate | 92% | 0.854 | 0.471 | 2 |
| Id-i | 2-methylpyrimidine-5-carboxylate | 99% | 2.85 | 0.96 | 3 |
| Ic-ii | 4-methylthiazol-2-yl carbamate | 97% | 25.17 | 20.58 | 2 |
| Ic-iii | 5-methylpyrazin-2-yl carbamate | 97% | 35.75 | 14.86 | 9 |
| Ic-iv | 2-methylpyrimidin-5-yl carbamate | 98% | 79.13 | 21.63 | 3 |
| Ic-v | 5-methylisoxazol-3-yl carbamate | 97% | 117.6 | 38.6 | 7 |
| Id-ii | 6-chloropyridine-3-carboxylate | 98% | 372.7 | 187.5 | 5 |
| Id-iii | 4-methylthiophene-2-carboxylate | 99% | 377.4 | 84.47 | 6 |
| — | 2-ethylpyrimidine-5-carboxylate | 99% | 916.7 | 288.3 | 2 |

TABLE 1B-continued

Salvinorin Derivatives

| Formula | R¹ | Efficacy | Potency (nM) | SEM (nM) | N |
|---|---|---|---|---|---|
| — | 5-methylpyrazine-2-carboxylate | 98% | 1278 | 82.5 | 2 |
| — | (5-methylthiazol-2-yl)carbamate | 103% | 1284 | 277 | 2 |
| — | 5-methylisoxazole-3-carboxylate | 97% | 1754 | 563 | 4 |
| — | isoxazole-3-carboxylate | 104% | 3778 | 1087 | 3 |
| — | 4-methyloxazole-2-carboxylate | 103% | 5991 | 1711 | 2 |
| — | (2-ethylpyrimidin-5-yl)carbamate | 88% | 7464 | 2536 | 2 |

The "β-arrestin Recruitment EC$_{50}$±SEM" column in Table 2 below represents the degree to which each tested compound recruited beta-arrestin to interact with uOR. As will be appreciated by those skilled in the art, EC$_{50}$ refers to the concentration of a drug which induces a response halfway between the baseline and maximum after a specified exposure time. In this instance, lower values indicate greater potency of the molecule, and this is less desirable. This indicates that the β-arrestin receptor is recruited at lower dose of the tested compound, which could potentially result in receptor desensitization and other undesirable side effects. The molecules shown with ED50 approximately (or larger than) 10 uM are essentially non-pharmacologic—highly desirable relative to receptor desensitization. EC$_{50}$ in Table 2 below is expressed in nanomolar units (nM), where 1 M is equivalent to 1 mol/L.

As will also be understood by those skilled in the art, "Max Fold Efficacy" refers to the maximum signal/background ratio that an agonist will induce or, conversely, that an antagonist will inhibit an agonist from inducing a response. In Table 2 below, the "Max Fold Efficacy" column indicates the strength of the signal increase over the control/background measurement for uOR receptor internalization at the E.C. 50. A lower value indicates a lower level of specific β-arrestin recruitment, which is also consistent with the very high EC50 as it relates to a lower potential for receptor internalization, tolerance, and other side effects.

TABLE 2A

Standard Opioid Receptor Agonists

| Formula | R¹ | EC50 ± SEM (nM) | Max Fold Efficacy | N |
|---|---|---|---|---|
| — | Met-Enkephalin | 441.1 ± 38.81 | 38.3 | 4 |
| — | DAMGO | 176.3 ± 18.19 | 38.4 | 16 |
| — | Morphine | 458.1 ± 39.96 | 10 | 7 |

TABLE 2B

| Formula | R¹ | EC50 ± SEM | Max Fold Efficacy | N |
|---|---|---|---|---|
| — | benzamide | 9190 ± 2749 | 21.73 | 7 |
| Ia-i | 4-cyanophenyl carbamate | 9847 ± 152.8 | 9.5 | 4 |
| Ia-ii | 4-methylphenyl carbamate | >10 µM | 8.8 | 2 |
| Ia-iii | 4-chlorophenyl carbamate | >10 µM | 7.6 | 5 |
| Ia-iv | 4-fluorophenyl carbamate | >10 µM | 4.3 | 2 |
| Ia-v | 4-(difluoromethoxy)phenyl carbamate | >10 µM | 9.5 | 3 |
| Ia-vi | 4-(trifluoromethyl)phenyl carbamate | >10 µM | 5.1 | 3 |
| Ia-vii | 3,4-difluorophenyl carbamate | >10 µM | 2.2 | 2 |
| Ia-viii | 4-chloro-2-fluorophenyl carbamate | >10 µM | 2.3 | 2 |
| Ib-i | benzoyl urea | >10 µM | 3.14 | 2 |

TABLE 2B-continued

Salvinorin Derivatives

| Formula | R¹ | EC50 ± SEM | Max Fold Efficacy | N |
|---|---|---|---|---|
| Ib-ii | benzoyl carbamate (PhC(O)NHC(O)O–) | >10 μM | 4.8 | 3 |
| — | 4-(trifluoromethyl)benzoate | >10 μM | 9.3 | 3 |
| — | benzoate | >10 μM | 2.4 | 5 |
| — | phenyl carbamate (PhNHC(O)O–) | >10 μM | 3.4 | 3 |
| — | 4-fluorobenzoate | >10 μM | 2.2 | 3 |
| — | 3,4-dichlorophenyl carbamate | >10 μM | 5.8 | 2 |
| — | 4-(trifluoromethylthio)phenyl carbamate | >10 μM | 2.3 | 1 |
| — | 4-methoxybenzoate | >10 μM | 3.1 | 2 |
| — | 4-cyanophenyl urea | >10 μM | 1.16 | 2 |
| — | 4-bromobenzoate | >10 μM | 2.7 | 2 |

TABLE 2B-continued

Salvinorin Derivatives

| Formula | R¹ | EC50 ± SEM | Max Fold Efficacy | N |
|---|---|---|---|---|
| — | 4-chlorophenyl sulfonylurea | >10 μM | 1.2 | 2 |
| Ic-i | 2-methylthiazol-4-yl carbamate | 2070 ± 649 | 31.3 | 12 |
| Id-i | 2-methylpyrimidine-5-carboxylate | >10 μM | 4.2 | 3 |
| Ic-ii | 4-methylthiazol-2-yl carbamate | >10 μM | 3.8 | 2 |
| Ic-iii | 5-methylpyrazin-2-yl carbamate | >10 μM | 9.5 | 4 |
| Ic-iv | 2-methylpyrimidin-5-yl carbamate | >10 μM | 2.8 | 3 |
| Ic-v | 5-methylisoxazol-3-yl carbamate | >10 μM | 2.4 | 3 |
| Id-ii | 6-chloropyridine-3-carboxylate | >10 μM | 9.3 | 4 |
| Id-iii | 4-methylthiophene-2-carboxylate | >10 μM | 6.1 | 4 |
| — | 2-ethylpyrimidine-5-carboxylate | >10 μM | 5.1 | 2 |

TABLE 2B-continued

Salvinorin Derivatives

| Formula | R[1] | | EC50 ± SEM | Max Fold Efficacy | N |
|---|---|---|---|---|---|
| — | (5-methylpyrazine-2-carboxylate structure) | | >10 μM | 1.8 | 2 |
| — | (5-methylthiazol-2-yl carbamate structure) | | >10 μM | 2.6 | 2 |
| — | (5-methylisoxazole-3-carboxylate structure) | | >10 μM | 1.3 | 3 |
| — | (isoxazole-3-carboxylate structure) | | >10 μM | 1 | 5 |
| — | (4-methyloxazole-2-carboxylate structure) | | >10 μM | 1.1 | 2 |
| — | (2-ethylpyrimidin-5-yl carbamate structure) | | >10 μM | 1.5 | 2 |

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A compound of Formula Ib or a salt thereof,

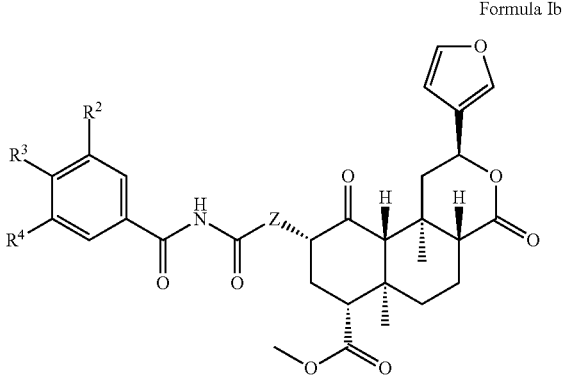

Formula Ib wherein

R², R³, and R⁴ are each independently selected from the group consisting of hydrogen, halogen, $CH_3$, CN, $O(CHF_2)$, $CF_3$, $OCH_3$, and $OCF_3$;

and Z is selected from the group consisting of O and NH.

2. The compound of claim 1 wherein R², R³, and R⁴ are each hydrogen.

3. A compound of Formula Ic or a salt thereof,

Formula Ic

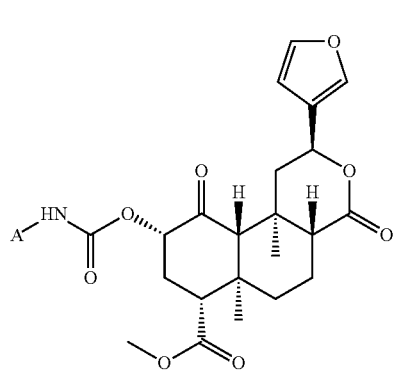

wherein A is a heteroaryl selected from the group consisting of pyridyl, pyrimidyl, pyrazyl, thiazyl, thienyl, isoxazolyl, oxazolyl, and furanyl, each of which is substituted with one or more substituents independently selected from the group consisting of halogen, $CH_3$, CN, $O(CHF_2)$, $CF_3$, $OCH_3$, and $OCF_3$.

4. The compound of claim 3 wherein A comprises at least one trans substituent.

5. A compound selected from the group consisting of:

Formula Ia-i, or a salt thereof,

Formula Ia-i

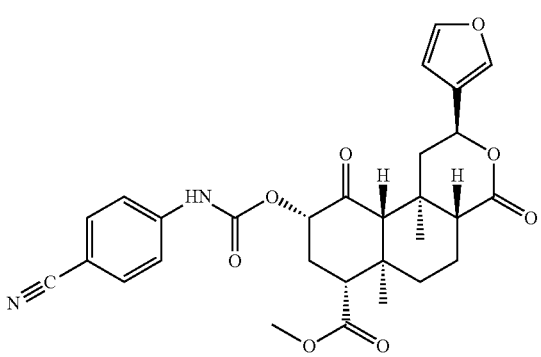

Formula Ia-ii, or a salt thereof,

Formula Ia-ii

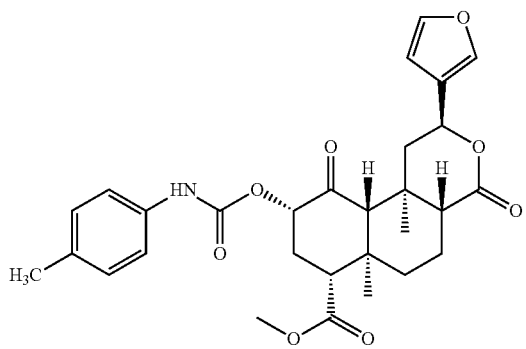

Formula Ia-iii, or a salt thereof,

Formula Ia-iii

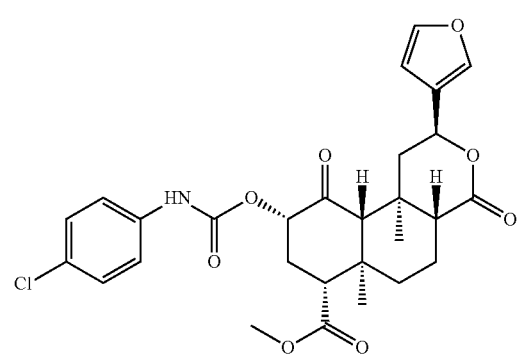

Formula Ia-iv, or a salt thereof,

Formula IA-iv

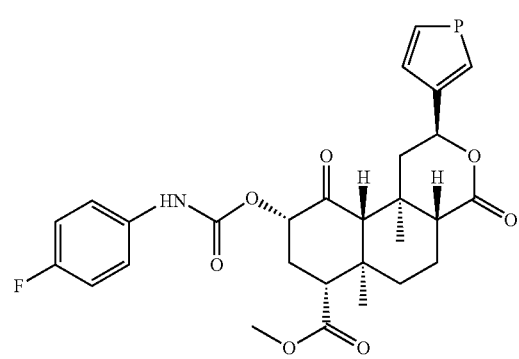

Formula Ia-v, or a salt thereof,
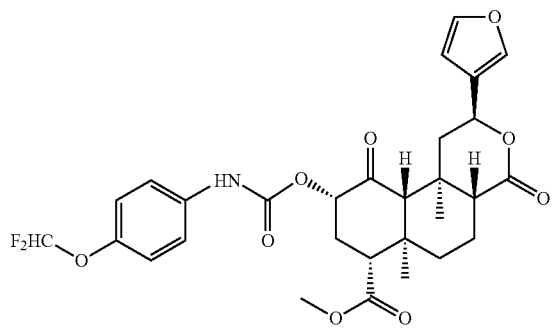
Formula Ia-v
Formula Ia-vi, or a salt thereof,
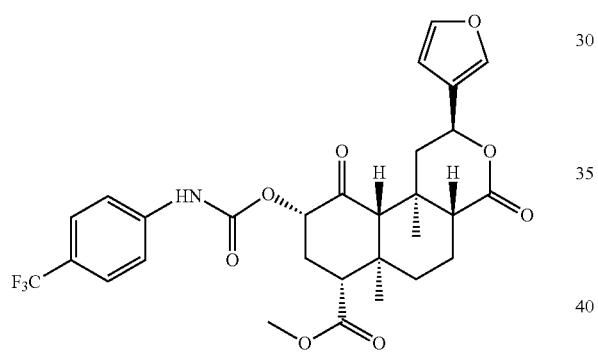
Formula Ia-vi
Formula Ia-vii, or a salt thereof,
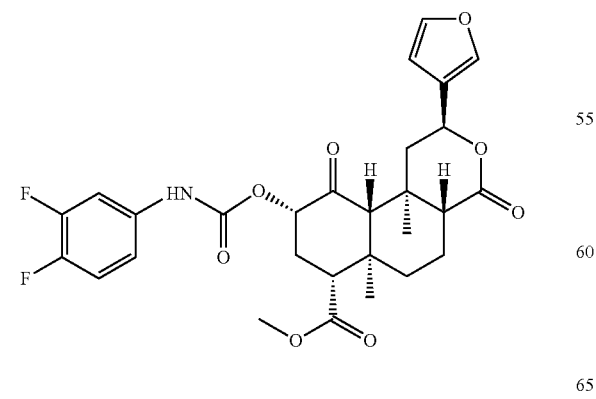
Formula Ia-vii
Formula Ia-viii, or a salt thereof,
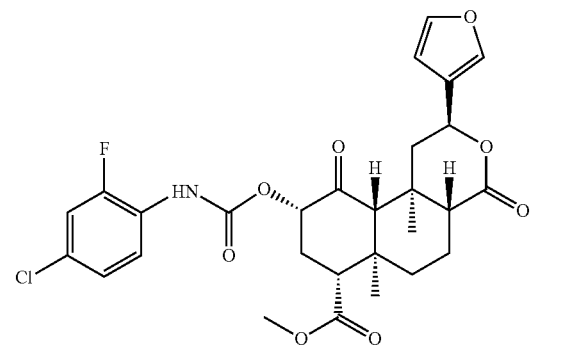
Formula Ia-viii
Formula Ib-i, or a salt thereof,
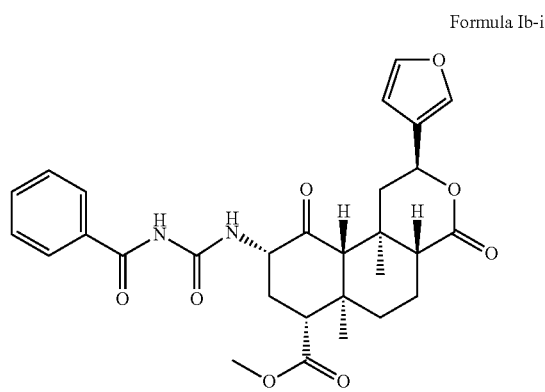
Formula Ib-i
Formula Ib-ii, or a salt thereof,
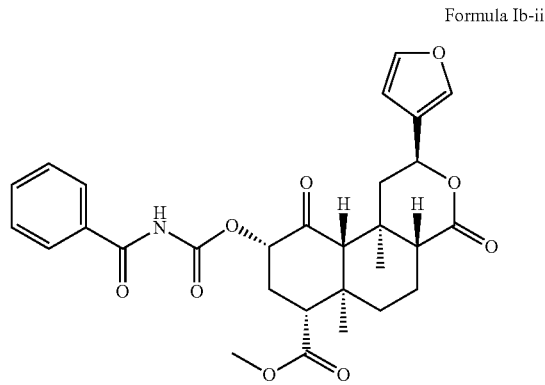
Formula Ib-ii Formula Ic-i, or a salt thereof,
Formula Ic-i
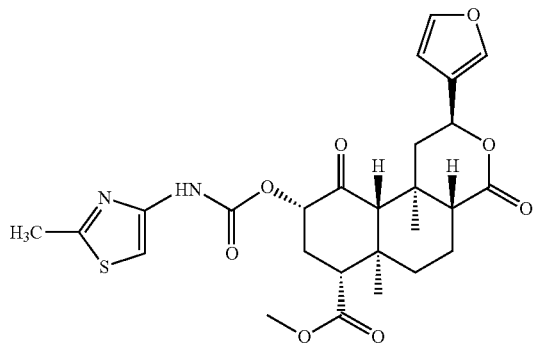
Formula Ic-ii, or a salt thereof,
Formula Ic-ii
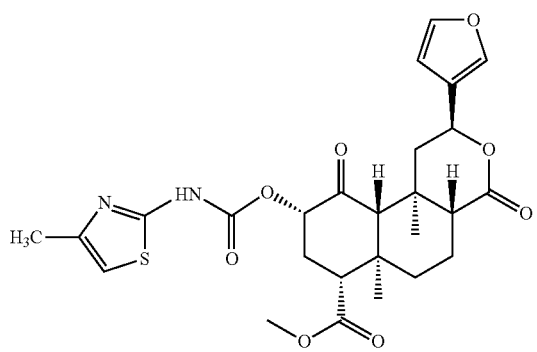
Formula Ic-iii, or a salt thereof,
Formula Ic-iii
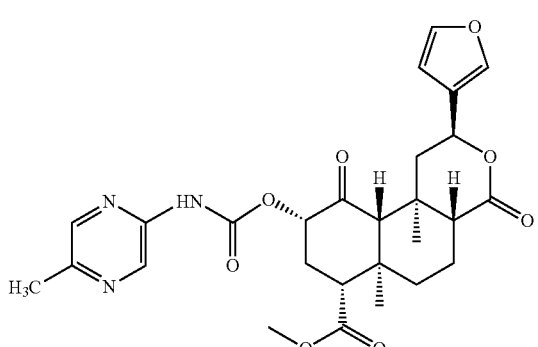
Formula Ic-iv, or a salt thereof,
Formula Ic-iv
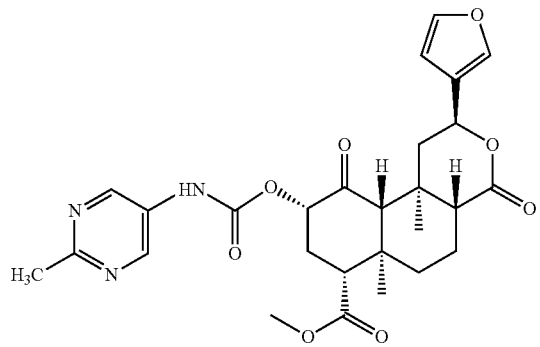
Formula Ic-v, or a salt thereof,
Formula Ic-v
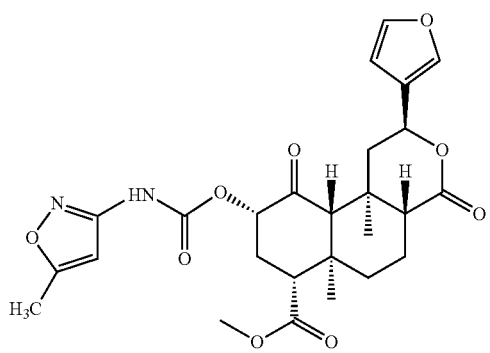
Formula Id-i, or a salt thereof,
Formula Id-i
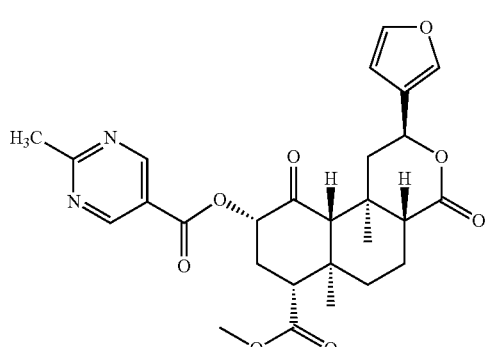

Formula Id-ii, or a salt thereof,

Formula Id-ii

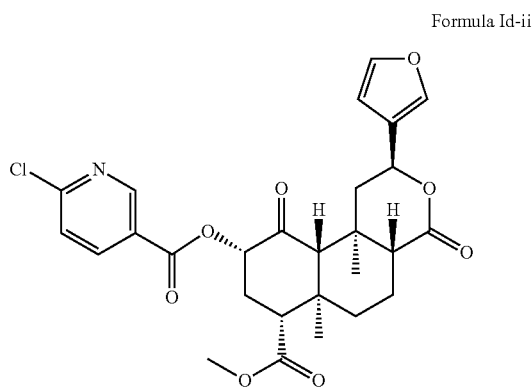

and Formula IId-iii, or a salt thereof

Formula IId-iii

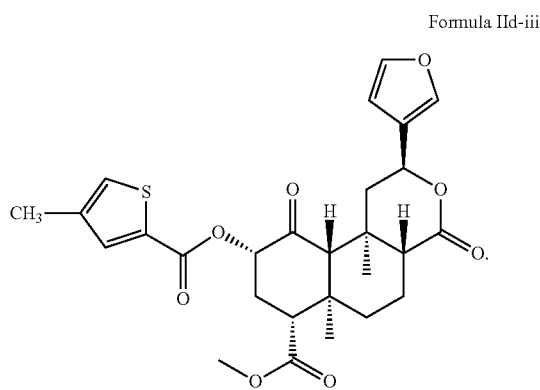

6. The compound of claim 1, wherein the compound is a μ-opioid receptor agonist having an efficacy at least about 90% as compared to DAMGO.

7. The compound of claim 1, wherein the compound is a μ-opioid receptor agonist having a potency of less than about 600 nM when evaluated using the experimental procedure described in Example 2.

8. The compound of claim 1, wherein the compound exhibits a mean β-arrestin recruitment EC50 of at least about 9 μM.

9. The compound of claim 1, wherein the compound exhibits a β-arrestin recruitment maximum-fold efficacy signal versus background of less than about 6.

10. A pharmaceutical composition comprising:
    (a) the compound of claim 5; and
    (b) at least one pharmaceutically acceptable excipient.

11. A method of treating pain in a mammal, the method comprising administering the compound of claim 5 to a human in need of treatment for pain.

12. The compound of claim 5 wherein the compound is Formula Ia-i, or a salt thereof.

13. The compound of claim 5 wherein the compound is Formula Ia-ii, or a salt thereof.

14. The compound of claim 5 wherein the compound is Formula Ia-iii, or a salt thereof.

15. The compound of claim 5 wherein the compound is Formula Ia-iv, or a salt thereof.

16. The compound of claim 5 wherein the compound is Formula Ia-v, or a salt thereof.

17. The compound of claim 5 wherein the compound is Formula Ia-vi, or a salt thereof.

18. The compound of claim 5 wherein the compound is Formula Ia-vii, or a salt thereof.

19. The compound of claim 5 wherein the compound is Formula Ia-viii, or a salt thereof.

20. The compound of claim 5 wherein the compound is Formula Ib-i, or a salt thereof.

21. The compound of claim 5 wherein the compound is Formula Ib-ii, or a salt thereof.

22. The compound of claim 5 wherein the compound is Formula Ic-i, or a salt thereof.

23. The compound of claim 5 wherein the compound is Formula Ic-ii, or a salt thereof.

24. The compound of claim 5 wherein the compound is Formula Ic-iii, or a salt thereof.

25. The compound of claim 5 wherein the compound is Formula Ic-iv, or a salt thereof.

26. The compound of claim 5 wherein the compound is Formula Ic-v, or a salt thereof.

27. The compound of claim 5 wherein the compound is Formula Id-i, or a salt thereof.

28. The compound of claim 5 wherein the compound is Formula Id-ii, or a salt thereof.

29. The compound of claim 5 wherein the compound is Formula IId-iii, or a salt thereof.

* * * * *